United States Patent [19]

Zardi et al.

[11] Patent Number: 5,756,048
[45] Date of Patent: May 26, 1998

[54] MODERNIZATION OF A REACTOR

[75] Inventors: Umberto Zardi, Breganzona; Giorgio Pagani, Viale Faenza, both of Italy

[73] Assignee: Methanol Casale, S.A., Lugano-Besso, Switzerland

[21] Appl. No.: 375,985

[22] Filed: Jan. 20, 1995

[30] Foreign Application Priority Data

Jan. 20, 1994 [CH] Switzerland ............... 00 169/94

[51] Int. Cl.⁶ ............................................. B01J 8/04
[52] U.S. Cl. ............... 422/49; 422/191; 422/194; 422/311
[58] Field of Search ............... 422/191, 194, 422/201, 207, 311, 148, 49

[56] References Cited

U.S. PATENT DOCUMENTS

| | | | |
|---|---|---|---|
| 2,646,391 | 7/1953 | Houdry | 422/191 |
| 3,208,833 | 9/1965 | Carson | 422/191 |
| 3,211,641 | 10/1965 | Hailik et al. | 422/191 |
| 3,235,344 | 2/1966 | Dreyer et al. | 422/191 |
| 3,592,613 | 7/1971 | Boyd | 422/191 |
| 3,723,072 | 3/1973 | Carson et al. | 422/194 |
| 4,248,832 | 2/1981 | Aiken et al. | 422/191 |
| 4,311,671 | 1/1982 | Notman | 422/194 |
| 4,755,362 | 7/1988 | Zardi | 422/148 |
| 4,952,375 | 8/1990 | Zardi | 422/191 |

FOREIGN PATENT DOCUMENTS 0359952  3/1990  European Pat. Off.

*Primary Examiner*—Krisanne Thornton
*Attorney, Agent, or Firm*—Sughrue, Mion, Zinn, Macpeak & Seas, PLLC

[57] ABSTRACT

A method for in-situ modernization of a reactor for carrying out heterogeneous exothermic synthesis reactions, in particular of the so-called lozenge type including an external shell (2), calls for prearrangement within the shell (2) of a plurality of superimposed catalyst beds (12, 13, 14) supported at a pre-set distance by means of support elements (22, 23, 24) rested on or fixed to, e.g. by welding, a plurality of annular shoulders (8a, 8b, 8c) pre-existing in the reactor.

5 Claims, 4 Drawing Sheets

MODERNIZATION OF A REACTOR

DESCRIPTION

1. Field of the Invention

The present invention relates to a method for in-situ modernization of a reactor for carrying out heterogeneous exothermic synthesis reactions, in particular of the so-called lozenge type, including an external shell, at least one catalyst bed in said shell and at least one cooling gas distributor supported in the catalyst bed by an annular shoulder extending from the shell.

More specifically, the present invention relates to a modernization method of the type comprising the step of providing in said shell a plurality of superimposed catalyst beds in mutually spaced relationship.

In the description given below and in the following claims, the term: "in-situ" modernization, is understood to mean the on-site modification of a pre-existing reactor in order to improve its performance and obtain e.g. a production capacity and/or a conversion yield comparable to those of a newly-built reactor.

In the terminology of the field this type of modernization is also termed retrofitting or revamping.

As is known, in the field of heterogeneous exothermic synthesis reactions in general and, more specifically, in the methanol production, it is necessary to satisfy a two-fold need, i.e. to increase the production capacity of pre-existing synthesis reactors on the one hand and, on the other hand, to achieve an improvement of the conversion yield and a reduction of the reactor energy consumption.

2. Known Art

For the purpose of satisfying the above-identified need, the so-called technique of modernizing the pre-existing reactors, aiming at avoiding a costly replacement of the latter and achieving at the same time the maximum conversion compatible with the available catalyst volumes, has become increasingly accepted.

As to the modernization of heterogeneous exothermic synthesis reactors of the so-called "lozenge" or "ICI" type, i.e. including a single catalyst bed in which a plurality of "lozenge-shaped" distributors for the cooling gases is inserted, a first method proposed in the art calls for replacement of said single bed by a plurality of catalyst beds superimposed and in mutually spaced relationship, as described e.g. in European patent application EP-A-0 359 952 of the same Applicant.

In accordance with said method, the bottom of each catalyst bed is laid directly on the annular supporting shoulders of the aforementioned lozenge distributors, while new distributors of cold reagent gases are inserted between the various catalyst beds to perform the necessary intermediate cooling.

Although an increase in production capacity and a reduction of energy consumption of the pre-existing reactor are achieved, the need of maintaining as far as possible unaltered the structure of the reactor and in particular its external shell, does not allow to achieve an optimal distribution of the catalyst volumes inside the synthesis reactor.

Just because of this need, in fact, the position of the new catalyst beds and, hence, the distribution of the catalyst volumes inside the reactor cannot be performed at will.

As a result, the modernized reactor in accordance with the teachings of the known art can reach a conversion yield lower than that which could be reached by an optimal use of the volume theoretically available within the reactor.

SUMMARY OF THE INVENTION

The technical problem underlying the present invention is, therefore, that of providing a method of modernizing a heterogeneous exothermic synthesis reactor, in particular—but not exclusively—of the so-called "lozenge" type, which allows an optimal distribution of the catalyst volumes within the synthesis reactor, thereby further increasing the conversion yield and/or the production capacity over those obtainable by the modernization methods in accordance with the above-mentioned prior art.

This problem is solved by a method of the type set forth above, wherein at least one of said catalyst beds is provided in the shell at a predetermined distance from the remaining beds by means of at least one support assembly rested on or fixed to said at least one annular shoulder.

Advantageously, the method of the present invention allows the arrangement of the catalyst beds according to the optimal catalyst distribution for the specific reactor considered, so as to make the best possible use of the available volume.

In accordance with the present invention, the supporting assemblies of the beds may be merely rested on the above-mentioned annular shoulders or may be fixed thereto permanently, e.g. by welding.

In accordance with the method of the present invention, an optimal distribution of the catalyst volume within the reactor can be achieved by using the annular shoulder—among the pre-existing ones—which proves to be in the most appropriate position for the size of the bed to be supported.

Thus, for example, depending on the relative position between the bottom of the bed and the annular supporting shoulder, the above-mentioned support assemblies can fulfill their supporting function in two ways, acting substantially as struts, i.e. compressed by the weight of the bed when they extend beneath the bottom thereof, and acting substantially as tie rods, i.e. tensioned by the weight of the bed, when they extend over the bottom thereof.

In this second case, the bed is "hung" on the annular shoulder on which the associated support assemblies are rested or fixed.

The advantage of supporting the catalyst beds in the most appropriate position allows in particular, differently from the known art, the introduction of a further amount of catalyst in the head zone of the reactor, up to a point near the feed opening of the reagent gases.

Clearly, the length of each support element can be determined by anyone skilled in the art depending on the structural characteristics of the reactor to be modernized (such as e.g. height and position of the supporting annular shoulders), on the characteristics of the catalyst employed for carrying out the heterogeneous synthesis reaction and on the conversion yield or production capacity required.

In accordance with the present invention, the values of the latter can be advantageously increased thanks to an optimal use of the space available within the synthesis reactor.

According to the present invention, the supporting elements of the support assemblies for the catalyst beds have a shape which best suits the positioning requirements within the reactor, either as struts or tie rods resting on the pre-existing annular shoulders. Thus, for example, said supporting elements may have an essentially tubular shape, so as to conform to the cylindrical symmetry of the synthesis reactor.

In a preferred embodiment of the present modernization method, each catalyst bed is supported in the reactor by means of a respective supporting assembly comprising a plurality of essentially cylindrical rods spaced according to a pre-set pitch and supported on the above-mentioned annular shoulders.

If the beds are hung on the annular shoulders, these rods are equipped with appropriately hook-shaped ends respectively engaging with the bottom of the bed and resting on the chosen shoulder for support of the bed.

In accordance with the present invention, the various catalyst beds provided in the reactor can be crossed by the various reaction mixtures either with axial flow or with radial or axial-radial flow.

In a preferred embodiment, the catalyst beds are axially crossed by the gaseous mixtures except the last one, which is traversed by an axial-radial flow with a further advantageous reduction of energy consumption due to a reduced pressure drop across the bed.

The characteristics and advantages of the present invention are set forth in the description of an embodiment thereof given below by way of non-limiting example with reference to the annexed drawings.

DETAILED DESCRIPTION OF A PREFERRED EMBODIMENT

Figure 1:
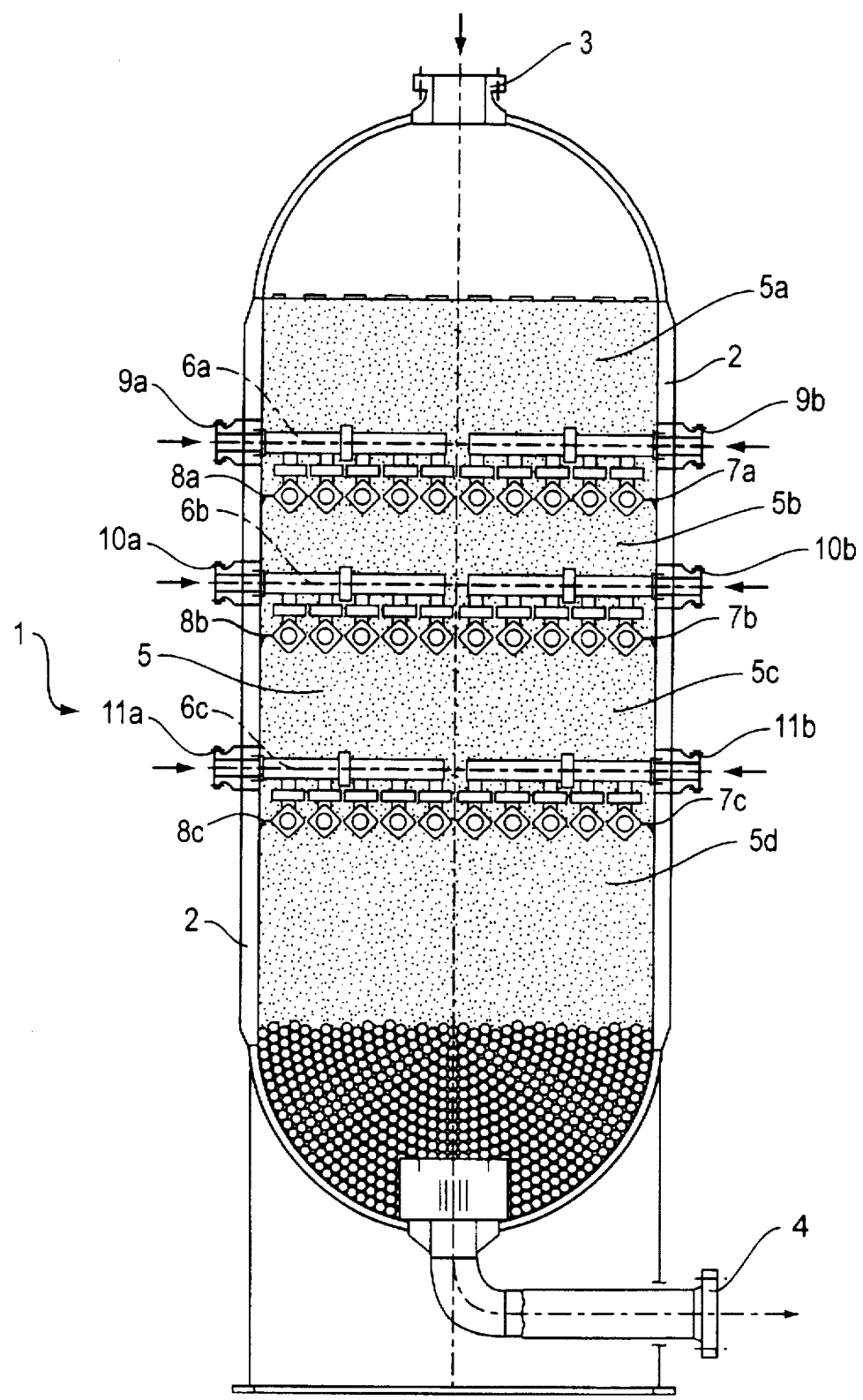
FIG. 1 shows a longitudinal cross section of a conventional reactor of the so-called "lozenge" type for carrying out heterogeneous exothermic synthesis reactions.

With reference to FIG. 1, reference number 1 indicates a reactor of the so-called lozenge type for carrying out heterogeneous exothermic synthesis reactions at medium pressure (60–100 bar) e.g. for methanol production.

The reactor 1 comprises a tubular shell or jacket 2 quipped on opposite sides with inlet and outlet openings 3, 4 respectively for feeding reagent gases and withdrawing reaction products and wherein a single catalyst bed 5 is supported.

The bed 5 is conventionally divided into four portions 5a–5d through three distributors 6a–6c of cold quenching gases extending in parallel spaced relationship within the bed at pre-set distances.

In correspondence to each distributor, the shell 2 is provided on opposite sides with a plurality of openings indicated by reference numbers 9a–11a and respectively 9b–11b.

Each of the distributors 6a–6c comprises a plurality of transverse lozenge-shaped chambers 7a–7c, for mixing the quenching gases with the gases flowing through the catalyst bed 5 and is supported by the shell 2 through respective annular shoulders 8a–8c.

Figure 2:
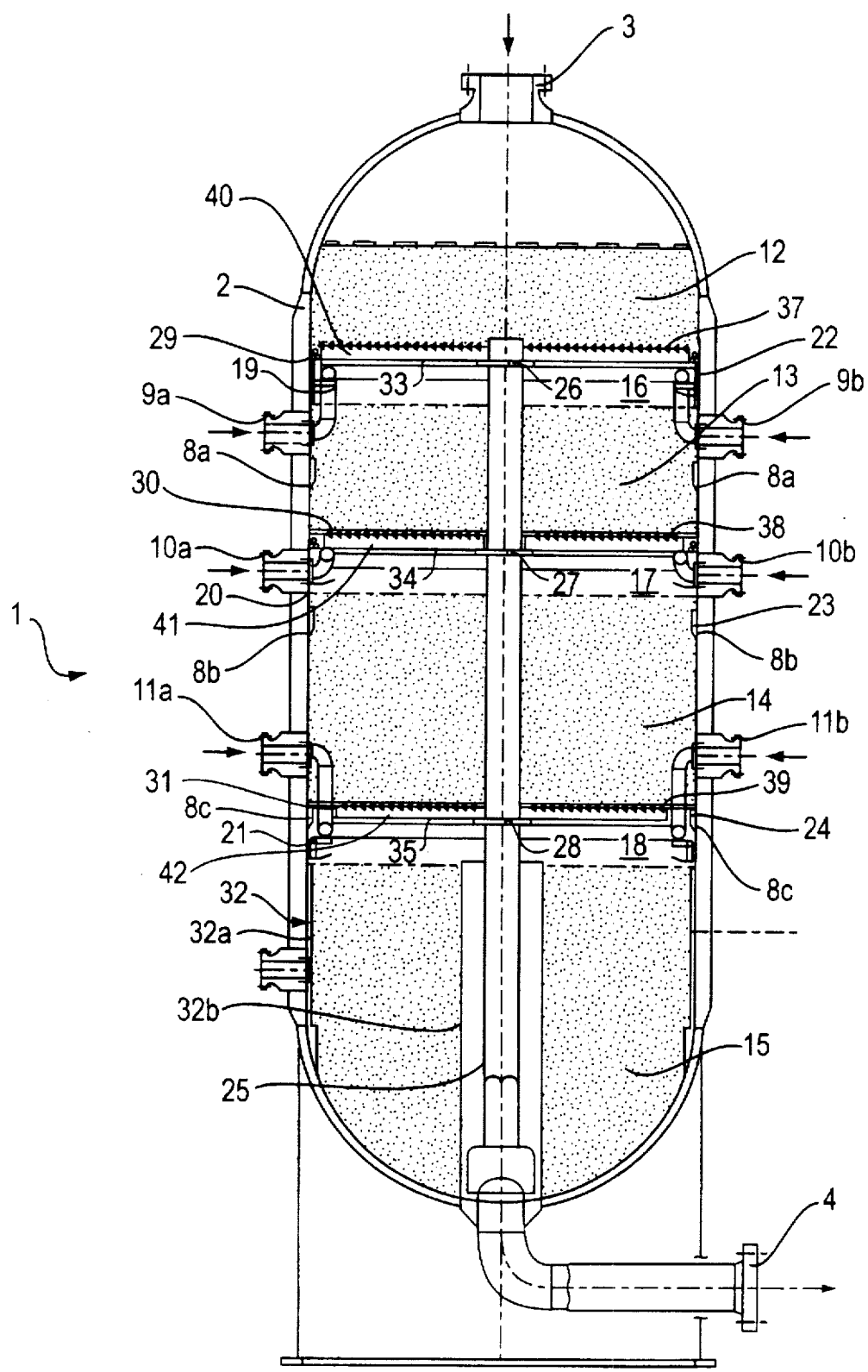
FIG. 2 shows a longitudinal cross section of a reactor obtained by modifying the lozenge reactor of FIG. 1 by the modernization method object of the present invention.
Figure 3:
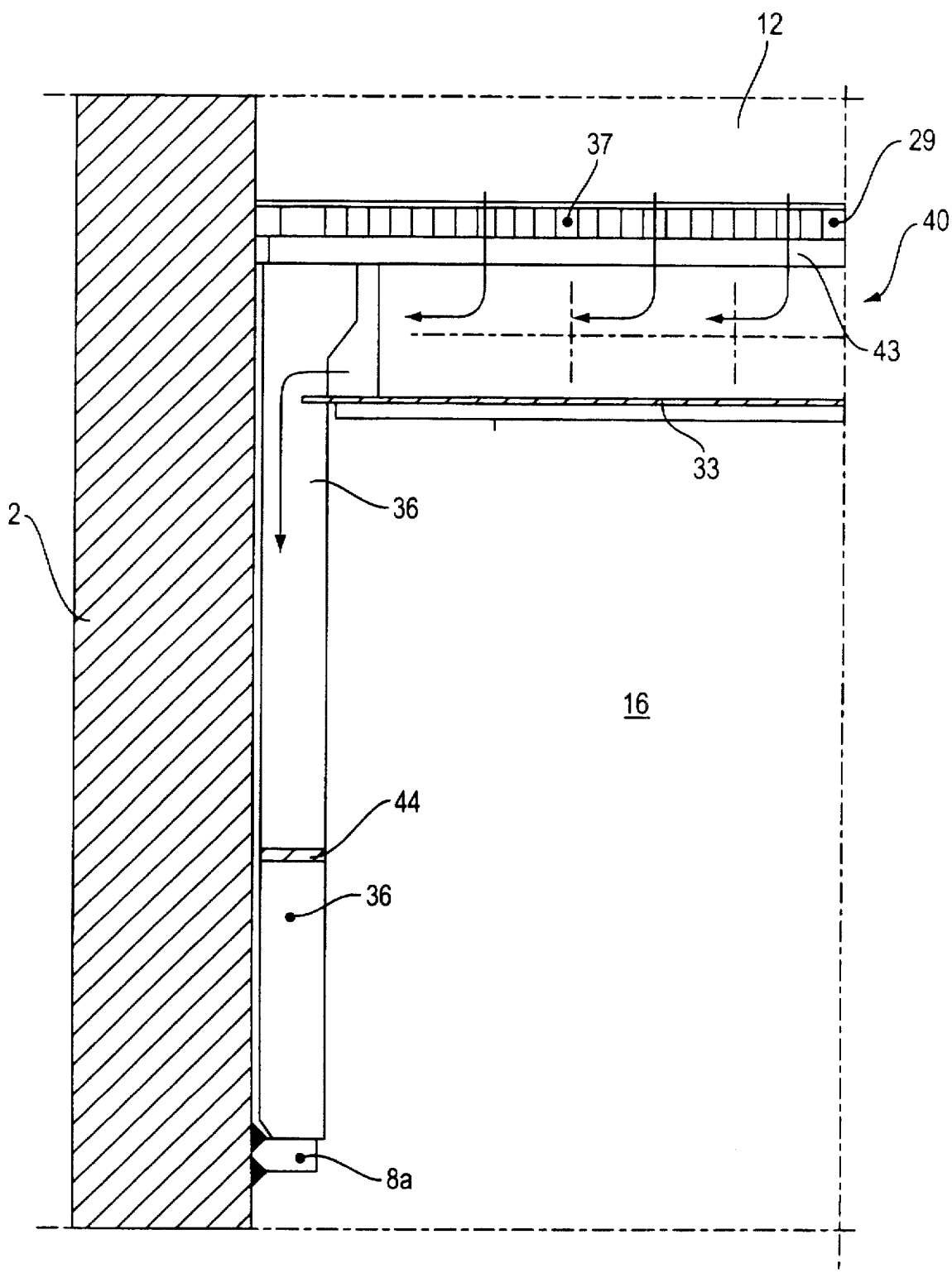
FIG. 3 shows a front elevational view, in enlarged scale and in partial cross section, of some details of the reactor of FIG. 2.

FIG. 2 shows a heterogeneous exothermic synthesis reactor obtained by modifying the reactor of FIG. 1 by means of a modernization method in accordance with the present invention.

In said figure, the details of reactor 1 structurally and functionally equivalent to those illustrated in FIG. 1 are indicated by the same reference numbers and will not be further described.

In accordance with a preliminary step of the present method, the catalyst bed 5 of reactor 1 is removed and replaced with a plurality of superimposed catalyst beds 12, 13, 14 and 15.

According to the present invention, the catalyst beds 12–14 are supported in mutually spaced relationship in the shell 2 through respective support assemblies 22, 23 and 24 rested on the pre-existing annular shoulders 8a, 8b and 8c.

In a preferred embodiment, the beds 12, 13 and 14 are of the so-called axial flow type and are equipped with respective gas-permeable essentially annular bottoms 29, 30 and 31. The latter comprise in turn perforated plates or grates 37, 38 and 39 for containment of the catalyst, rested on respective support structures 40, 41 and 42.

Figure 4:
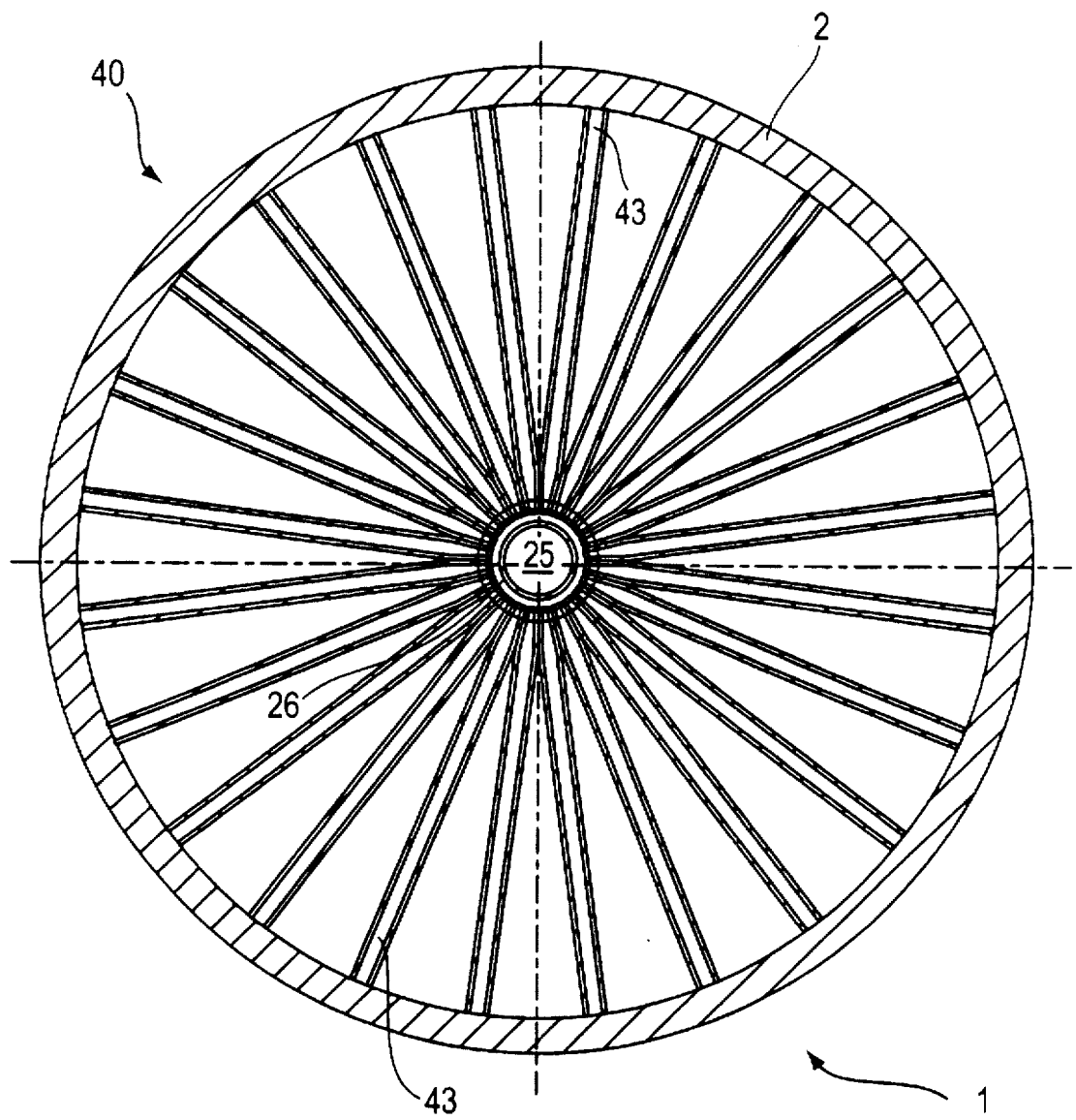
FIG. 4 shows a top view, in enlarged scale and in partial cross section, of additional details of the reactor of FIG. 2.

Preferably, the above-mentioned structures 40, 41 and 42 comprise a plurality of beams indicated by 43 in FIG. 4, extending radially in the shell 2 between a pipe 25 on which they are supported in a cantilevered manner on a plurality of annular shoulders 26, 27 and 28 and the support assemblies 22–24.

In this way, a plurality of essentially annular chambers 16, 17 and 18, designed to allow a thorough mixing between the gases emerging from each of the beds 12–14 and the cooling or quenching gases sent from the outside of the reactor 1, are defined in the shell 2.

In accordance with a preferred embodiment, the gas-permeable bottoms 29, 30 and 31, supporting the catalyst beds 12–14, comprise respective diaphragms 33, 34 and 35 extending from the pipe 25 near and below the supporting structures 40, 41 and 42.

In this manner, the reaction mixtures emerging from each of said beds are directed by the diaphragms 33–35 towards the internal wall of the shell 2 where they enter in intimate contact with the cooling or quenching gases.

Advantageously, the latter are introduced in the reactor 1 through toroidal distributors 19, 20 and 21 connected to the pre-existing openings 9a–11a, 9b–11b.

In accordance with a preferred embodiment of the invention, each of the support elements 22–24 comprises a plurality of essentially cylindrical rods 36 interconnected in spaced relationship by means of a supporting and stiffening ring 44.

The particular shape of the rods 36, which are preferably made of steel, is not critical. Preferably, however, the rods have a quadrangular or circular cross section.

In the modernization method of the present invention, the lower catalyst bed 15, which has greater volume, is preferably equipped with means, known per se, for obtaining a radial or axial-radial gas flow therethrough.

Said means may include e.g. an annular catalyst holding basket 32 equipped with opposed gas-permeable walls 32a, 32b respectively for gas inlet and outlet.

Means of this type for providing an axial-radial gas flow in the catalyst beds are described e.g. in U.S. Pat. No. 4,755,362 the description of which is incorporated herein by reference.

By means of the thus modernized reactor 1, a heterogeneous exothermic synthesis reaction, e.g. methanol synthesis, is performed by passing the gases through the catalyst beds 12–15 in a manner known per se.

In this concern, it should be noted that downstream of each of the catalyst beds 12–14, crossed with axial flow by the gaseous reaction mixtures, the reaction products are collected and intimately mixed with the quenching gases thanks to the presence of the diaphragms 33-35 and to the particular arrangement of the toroidal distributors 19-21.

Advantageously, said arrangement allows the achievement of a particularly effective mixing of the various hot and cold gases and optimal temperature control of the mixtures sent to the underlying catalyst bed where the synthesis reaction continues.

The final reaction products emerging from the last catalyst bed 15, traversed by a centripetal axial-radial flow, are finally withdrawn from the reactor 1 through the opening 4.

The method of the present invention allows an optimal distribution of the catalyst in the various beds, which are dimensioned in accordance with optimal design parameters even after entry in operation of the reactor.

It was also found that by providing the catalyst beds 12-14 at appropriate heights, it is possible to increase the total volume of catalyst which may be loaded into the synthesis reactor, thus further improving the conversion yield and/or the production capacity obtainable from the modernized reactor.

What is claimed is:

1. Method for in-situ modernization of a reactor for carrying out heterogeneous exothermic synthesis reactions including an external shell (2), a catalyst bed (5) in said shell (2) and at least one cooling gas distributor (6a, 6b, 6c) supported in said catalyst bed (5) by at least one annular shoulder (8a, 8b, 8c) extending from said shell (2), said method comprising the steps of:

providing in said shell (2) a plurality of superimposed catalyst beds (12, 13, 14, 15) in mutually spaced relationship wherein the beds are physically separated from each other; and supporting at least one of said catalyst beds (12, 13, 14, 15) in the shell (2) at a predetermined distance from an adjacent bed by means of at least one support assembly (22, 23, 24) comprised of a plurality of vertically disposed interconnected spaced apart support elements of a predetermined height supported on said at least one annular shoulder (8a, 8b, 8c), whereby an optimal catalyst distribution within the reactor is achieved.

2. Method according to claim 1, wherein each of said catalyst beds (12, 13, 14, 15) are supported in the shell (2) by a respective support assembly (22, 23, 24).

3. Reactor for carrying out heterogeneous exothermic synthesis reactions with optimal distribution of the catalyst volumes, comprising:

an external shell (2), wherein a plurality of superimposed catalyst beds (12, 13, 14) are supported in mutually spaced relationship;

a plurality of cooling gas distributors (19, 20, 21) each distributor being mounted between adjacent beds (12, 13, 14, 15), wherein said at least one of said catalyst beds (12, 13, 14) is supported at a predetermined distance from an adjacent bed by means of at least one support assembly (22, 23, 24) supported on annular shoulders (8a, 8b, 8c) extending in the shell (2) proximate to said cooling gas distributors (19, 20, 21);

said at least one support assembly being comprised of a plurality of vertically disposed interconnected spaced apart support elements extending between one of said annular shoulders and one of said catalyst beds.

4. Reactor according to claim 3, wherein said at least one support assembly (22, 23, 24) is integral with said annular shoulder (8a, 8b, 8c).

5. Reactor according to claim 3, wherein each of said at least one catalyst beds (12, 13, 14, 15) is supported within the shell by a respective support assembly (22, 23, 24).

* * * * *